US011439452B2

United States Patent
O'Connor (10) Patent No.: US 11,439,452 B2
(45) Date of Patent: Sep. 13, 2022

(54) SYSTEMS AND METHODS TO TREAT WOUNDS

(71) Applicant: UNITED STATES ENDOSCOPY GROUP, INC., Mentor, OH (US)

(72) Inventor: John P. O'Connor, Andover, MA (US)

(73) Assignees: CSA MEDICAL, INC., Lexington, MA (US); UNITED STATES ENDOSCOPY GROUP, INC., Mentor, OH (US)

( * ) Notice: Subject to any disclaimer, the term of this patent is extended or adjusted under 35 U.S.C. 154(b) by 809 days.

(21) Appl. No.: 16/043,356

(22) Filed: Jul. 24, 2018

(65) Prior Publication Data
US 2019/0029745 A1   Jan. 31, 2019

Related U.S. Application Data

(60) Provisional application No. 62/536,588, filed on Jul. 25, 2017.

(51) Int. Cl.
*A61B 18/02* (2006.01)
*A61B 18/00* (2006.01)

(52) U.S. Cl.
CPC ...... *A61B 18/0218* (2013.01); *A61B 2018/00005* (2013.01); *A61B 2018/00577* (2013.01); *A61B 2018/00791* (2013.01); *A61B 2018/0212* (2013.01); *A61B 2018/0262* (2013.01)

(58) Field of Classification Search
CPC ...... A61B 18/0218; A61B 2018/00005; A61B 2018/00577; A61B 2018/0079; A61B 2018/0212; A61B 2018/0262
See application file for complete search history.

(56) References Cited

U.S. PATENT DOCUMENTS

| | | | | |
|---|---|---|---|---|
| 6,027,499 | A  * | 2/2000 | Johnston | A61B 18/0218 |
| | | | | 600/104 |
| 2002/0143323 | A1* | 10/2002 | Johnston | A61B 34/35 |
| | | | | 606/21 |
| 2003/0032936 | A1* | 2/2003 | Lederman | A61B 18/1492 |
| | | | | 604/507 |
| 2009/0192505 | A1* | 7/2009 | Askew | A61M 16/0463 |
| | | | | 606/21 |
| 2010/0057065 | A1* | 3/2010 | Krimsky | A61B 18/0218 |
| | | | | 606/21 |
| 2010/0130970 | A1* | 5/2010 | Williams | A61M 25/10185 |
| | | | | 606/21 |
| 2011/0313411 | A1* | 12/2011 | Anderson | A61F 7/10 |
| | | | | 606/25 |
| 2013/0253491 | A1* | 9/2013 | Burr | A61B 18/0218 |
| | | | | 606/21 |
| 2015/0066005 | A1* | 3/2015 | Fan | A61B 18/0218 |
| | | | | 606/21 |

(Continued)

OTHER PUBLICATIONS

Vinnik, IuS, et al., "Application of cryogenic stimulation in treatment of chronic wounds", Vestnik khirurgii imeni I. I. Grekova (Vestn Khir Im Grek) Jan. 2008, 167(1): 27-28.

*Primary Examiner* — Michael F Peffley
*Assistant Examiner* — Amanda L Zink
(74) *Attorney, Agent, or Firm* — Calfee, Halter & Griswold LLP (57) ABSTRACT

The present disclosure relates generally to the field of cryoablation. In particular, the present disclosure relates to devices and methods for application of cryospray as a therapy to treat wounds.

20 Claims, 4 Drawing Sheets

(56) References Cited

U.S. PATENT DOCUMENTS

2015/0351822 A1* 12/2015 Mulcahey .......... A61B 18/0218
606/22
2019/0255281 A1* 8/2019 Mulcahey .......... A61B 18/0218

* cited by examiner

SYSTEMS AND METHODS TO TREAT WOUNDS

PRIORITY

This application claims the benefit of priority under 35 U.S.C. § 119 to U.S. Provisional Patent Application Ser. No. 62/536,588, filed Jul. 25, 2017, which is incorporated by reference herein in its entirety and for all purposes.

FIELD

The present disclosure relates generally to the field of cryoablation. In particular, the present disclosure relates to devices and methods for application of cryospray as a therapy to treat wounds.

BACKGROUND

Serious wounds, such as chronic wounds, can be difficult to treat and take extended periods of time to heal, exposing a patient to potential further complications. For example, a chronic wound may be described as a wound that has failed to complete a reparative process to produce functional and anatomic integrity within a three-month period or a healing process that has not established a sustained anatomic and functional result. It is estimated that over 6.5 million Americans are afflicted with chronic wound conditions. The cost of care of chronic wounds impacts the U.S. healthcare system by over $25 billion per year.

There are many approaches employed by clinicians to assist patients with chronic wounds. They range from the use of advanced dressings such as biatain foam, laser therapy, debridement, ultrasound therapy, antibiotics, growth factor therapy, sutures/staples, skin substitutes, negative pressure wound therapy, vacuum-assisted closure, hyperbaric oxygen treatment, ultraviolet light therapy, and topical wound treatments. These approaches have their various advantages and disadvantages.

There are some examples of the application of extreme cold as a cosmetic or dermatological treatment of skin surface tissue. Cryoprobes, as an example, with closed circulation of cryogen may be used to treat tissue, but require contact of the probes with the tissue, possibly resulting in the probe freezing to the tissue and/or causing other damage. Cryoprobes also cool tissue at a relatively slow rate that can tend to dehydrate the tissue, breakdown the cellular matrix and, in some instances, destroy cells may be useful to the reparative process.

Various advantages may therefore be realized by wound healing approaches of the present disclosure utilizing cryospray devices and methods, which may reduce the timing of wound healing, reduce symptoms, increase efficiency, and promote reepithelization of the tissue/skin.

SUMMARY

The present disclosure is generally directed to cryospray systems and methods for external use on the surface of a patient's body and internal use within the upper and lower GI tracts and respiratory system of the body, as well as systems and methods for possible use in a variety of other body passageways, organs and/or cavities, such as the vascular system, urogenital system, lymphatic system, neurological system and the like. Likewise, the present disclosure is useful for treatment of chronic wounds, and may by applicable as well for general categories of wounds, and other injured or damaged tissue, such as burns, ulcers, chronic wounds, lesions, to help ameliorate symptoms and spur rejuvenative healing.

In some embodiments, a method of treating a wound may include directing a distal tip of a cryospray catheter toward the wound, orienting the distal tip of the catheter at an angle relative to a surface of the wound, supplying cryogen to the distal tip of the catheter, and spraying cryogen from the distal tip onto a tissue region of the wound at a distance from the wound, at a temperature of the cryogen, and for a duration of spraying, which are sufficient for effective treatment of the tissue region. Spraying cryogen from a distal tip onto a tissue region of a wound may be at a distance ranging from about 10 mm to about 15 mm from the wound. A duration of spraying may be about 40 seconds. Spraying may be performed until a temperature of an approximate square surface of a tissue region of a wound, about 2 cm long by about 2 cm wide, is about −20° C. to a depth up to about 1 mm from the surface of the wound.

In some embodiments, a method of treating a wound may include effective treatment of a tissue region by cooling a region of the wound at more than about 50° C. per minute. Effective treatment of a tissue region may include forming intracellular ice crystals within a tissue region of a wound. Effective treatment of a tissue region may include maintaining an extracellular matrix of tissue within a tissue region of a wound. Effective treatment of a tissue region may include flash freezing a portion of a tissue region of a wound. Effective treatment of a tissue region may include remodeling at least a tissue region of a wound. Effective treatment of a tissue region may comprise ablating injured or damaged tissue within a tissue region of a wound. Effective treatment may include removal of tissue from a tissue region of a wound that has been treated.

In some embodiments, a method of treating a wound may include cryogen that may be liquid nitrogen, liquid argon, liquid oxygen, liquid nitrous oxide, and/or liquid carbon dioxide. A distal tip of a catheter may be oriented at an angle that is substantially perpendicular relative to a surface of a wound. A wound may be a burn, an ulcer, a chronic wound, and/or a lesion. Cryogen may be supplied to a distal tip of a catheter as a liquid and may convert to a gas spray as it exits. A temperature of the cryogen may range from about 0° C. to about −196° C.

In some embodiments, a method of treating a wound may include directing a distal tip of a cryospray catheter toward a wound, orienting the distal tip of the catheter at an angle relative to at least one surface layer of the wound, and spraying cryogen from the distal tip onto the at least one surface layer of the wound at a distance from the wound, at a temperature of the cryogen, and for a duration of spraying, which are sufficient for effective treatment of the at least one surface layer at a tissue temperature of about −20° C. up to a depth of about 1 mm. Cryogen may be sprayed until a temperature of an approximate square region of an at least one surface layer, about 2 cm long by about 2 cm wide, is about −20° C. to a depth up to about 1 mm. Effective treatment of a tissue region may include flash freezing an at least one surface layer. Effective treatment of a tissue region may include leaving a plurality of collagen fibers and an extra-cellular matrix of a region of a wound intact.

In some embodiments, a method of treating a wound may include inserting a cryospray catheter within a body lumen, orienting a distal tip of the catheter at an angle relative to a region of exposed tissue of a wound within the body lumen, supplying cryogen to the distal tip of the catheter, and spraying cryogen from the distal tip onto the exposed tissue region of the wound at a distance from the wound, at a temperature of the cryogen, and for a duration of spraying, which are sufficient for effective treatment of the tissue region. Effective treatment of an exposed tissue region may include ablating injured or damaged tissue. Spraying may include one or both of spraying cryogen from a distal tip of a catheter parallel to a longitudinal axis of the catheter, and spraying cryogen from a plurality of radial apertures at a distal tip of a catheter perpendicular to a longitudinal axis of the catheter.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

The present disclosure is not limited to the particular embodiments described. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure are described with specific reference to cryospray systems for external use on the surface of a patient's body and internal use within the upper and lower GI tracts and respiratory system of the body, it should be appreciated that such systems and methods may be used in a variety of other body passageways, organs and/or cavities, such as the vascular system, urogenital system, lymphatic system, neurological system and the like. Also, although embodiments may be described herein with specific reference to chronic wounds, the present disclosure is not limited to treatment of only chronic wounds. It is contemplated that the cryospray systems and methods of the present disclosure may by applicable to general categories of wounds, and as used herein, "wounds" refers to all manner of injured or damaged tissue, such as burns, ulcers, chronic wounds, lesions, etc.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As used herein, the term "distal" refers to the end farthest away from the medical professional when introducing a device near or into a patient, while the term "proximal" refers to the end closest to the medical professional when introducing a device near or into a patient. As used herein, "diameter" refers to the distance of a straight line extending between two points and does not necessarily indicate a particular shape.

The present disclosure generally provides for systems and methods to treat wounds using cryogen applied as a cryospray at a distance from wounds, e.g., from a catheter directed toward target tissue on the external surface of a body or from a catheter within a body lumen, as opposed to a closed end cryoprobe system where a probe would have to contact the wound, but the cryogen does not directly contact tissue. Exemplary cryosurgery systems in which the present disclosure may be implemented include, but are not limited to, those cryospray systems described in U.S. Pat. Nos. 9,301, 796 and 9,144,449, and U.S. patent application Ser. Nos. 14/012,320 and 14/869,814, each of which are herein incorporated by reference in their entirety.

In various embodiments, described here or otherwise, within the scope of the present disclosure, wounds may be treated through cryogenic spray therapy to help ameliorate chronic wound symptoms and to spur rejuvenative healing of impacted tissues. Cryospray therapy is a procedure in which wounded, diseased, damaged or otherwise damaged or injured tissue (collectively referred to herein as "target tissue") is treated by delivery of a cryogen spray under pressure. These systems are typically referred to as cryoablation systems, cryospray systems, cryospray ablation systems, cryosurgery systems, cryosurgery spray systems and/or cryogen spray ablation systems. As typically used, "cryogen" refers to any fluid (e.g., gas, liquefied gas or other fluid known to one of ordinary skill in the art) with a sufficiently low boiling point (i.e., below approximately −153° C.) for therapeutically effective use during a cryogenic surgical procedure. Suitable cryogens may include, for example, liquid argon, liquid nitrogen, liquid argon, liquid oxygen, and liquid helium. Pseudo-cryogens such as liquid carbon dioxide and liquid nitrous oxide that have a boiling temperature above −153° C. but still very low (e.g., −89° C. for liquid $N_2O$) may also be used. Cryogen spray may exit the cryogen delivery catheter at a temperature ranging from 0° C. to −196° C., causing the target tissue to freeze or "cryofrost."

In various embodiments, cryogenic spray may be applied to a wound that results in flash freezing of target tissue. This flash freezing may preserve the extracellular matrix of the target tissue. The flash freezing of the wound tissue may improve perfusion within the microcirculatory bed, thus enhancing cellular infiltration and the establishment of new vasculature that is critical to the repair process of the target tissue. Subsequently, epithelization and remodeling of the target tissue may be enhanced to enable transformation of a chronic condition to an acute condition.

In various embodiments, described here or otherwise, within the scope of the present disclosure, cryogenic spray may be applied to a wound in order to promote a rejuvenative healing response in the target tissue. Because collagen and elastin fibers may be less sensitive to the effects of cryotherapy than are epithelial cells, the tissue structure may remain intact. Following the cryogenic spray procedure, healing of the tissue may commence effective treatment in a rejuvenative fashion with minimal scarring. The resistance of the collagen fibers to damage from freezing may be the basis for favorable healing. Although freezing through cryospray is not hemostatic for major vessels, it may be useful in microcirculatory vessels to help control the oozing of blood associated with a chronic wound.

In various embodiments, cryogenic spray may be applied to a wound resulting in a reduction of bleeding and/or moisture leakage/seepage. Frozen and/or cooled tissue may close off fluid openings in addition to lowering fluid viscosity. The cooling and or freezing may also have an anesthetic effect, numbing and reducing pain. Because of this numbing, the patient does not need sedation during the cryotherapy procedure and avoids the potential negative effects of anesthesia.

During operation of a cryotherapy system, a medical professional (e.g., clinician, technician, medical professional, surgeon etc.) directs a cryogen spray onto the surface of a treatment area via a cryogen delivery catheter. Should the target tissue be internal, the medical professional may target the cryogen spray visually through a video-assisted device or endoscope, such as a bronchoscope, colonoscope or ureteroscope.

In various embodiments of the present disclosure, devices and method of operation are described for cryospray treatment of wounds, wherein a wound may be treated by directing a distal tip of a cryospray catheter toward the wound. The distal tip of the catheter may be oriented at an angle relative to a surface of the wound. The distal tip of the catheter may be supplied with cryogen. The cryogen may be sprayed from the catheter onto a tissue region of the wound at a distance from the wound, at a temperature of the cryogen, and for a duration of spraying, which are sufficient for effective treatment of the tissue region.

Figure 1:
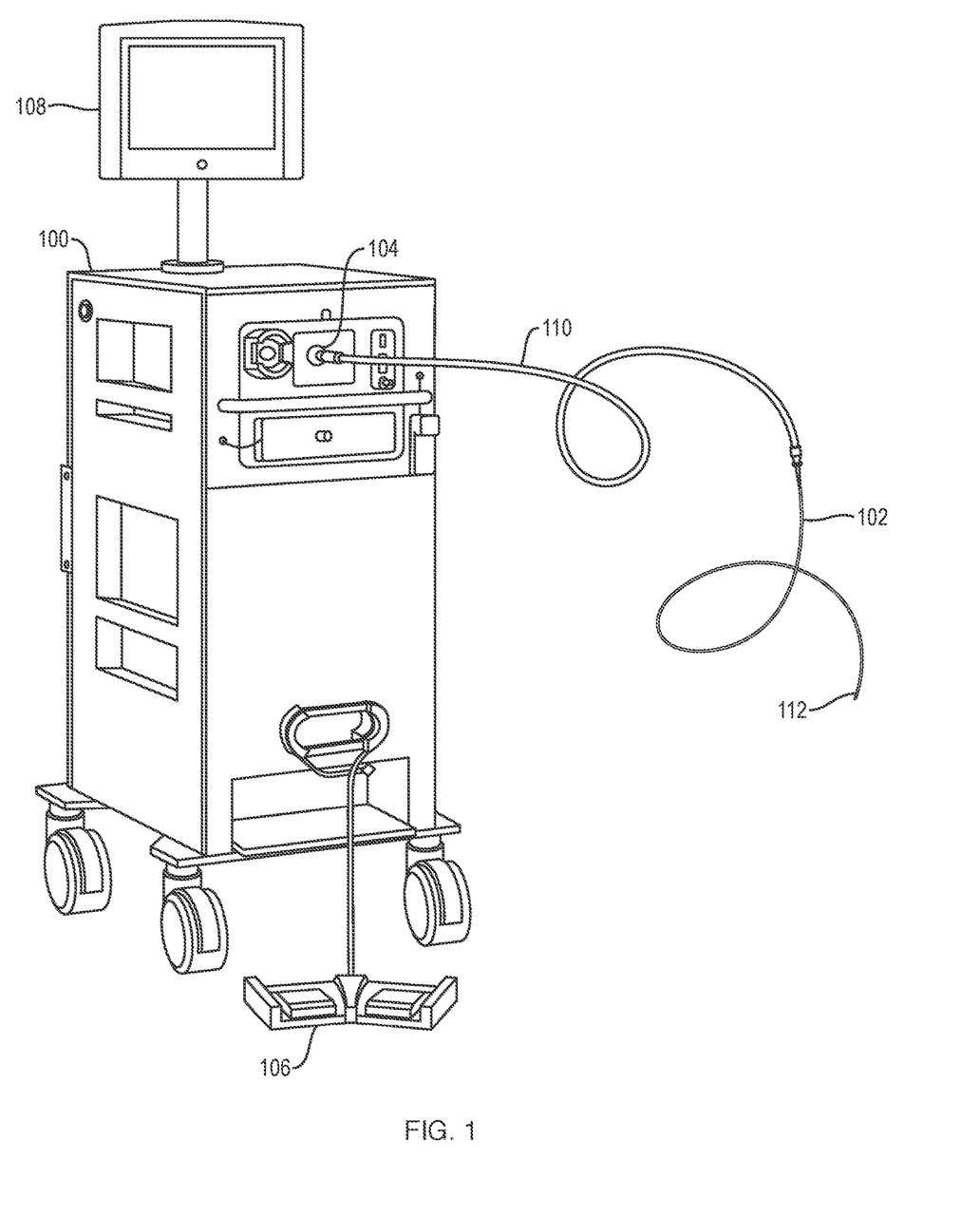
FIG. 1 illustrates an isometric view of a cryospray system in accordance with an embodiment of the present disclosure.

In one embodiment of a cyrospray delivery system suitable for delivery of a cryogen spray to treat wounds, as illustrated in FIG. 1, a catheter 102 is connected to a cryotherapy console 100 at a catheter interface 104. The catheter 102 may be used with an endoscope for delivery into a patient or may be used by itself outside of the patient for uses external to the body. If an endoscope is used, an image received at the lens on the distal end of the endoscope may be transferred to a monitoring camera which sends video signals via a cable to the monitor 108, where the procedure can be visualized. Built-in software and controls in the console allow the medical professional to control delivery of cryogen from the tank through the catheter 102 via a foot petal 106. The catheter 102 may have an insulated portion 110 and a distal tip 112.

As an example of the fluid mechanics of cyrospray formation and supply, with reference to the system illustrated in FIG. 1, as cryogen (e.g., liquid nitrogen) travels from the tank to the proximal end of cryogen delivery catheter 102, the liquid warms and starts to boil, resulting in cool gas emerging from the distal tip 112 of catheter 102. The amount of boiling in the catheter 102 depends on the mass, surface area, and thermal capacity of the catheter 102. When the liquid nitrogen undergoes a phase change from liquid to gaseous nitrogen, additional pressure is created throughout the length of catheter 102. This is especially true at a solenoid/catheter junction, where the diameter of the supply tube to the lumen of catheter 102 decreases, e.g., from approximately 0.25 inches to approximately 0.070 inches, respectively. The lumen of the catheter 102 may have a diameter, e.g., ranging between 0.030 and 0.100 inches. In an alternate embodiment, gas boiling inside the catheter 102 may be reduced even greater by the use of insulating materials such as PTFE, FEP, Pebax and the like to help reduce the temperature coefficient. The addition of PTFE is especially desirable if done in the inner lumen because its lower coefficient of friction aids in laminar flow of the fluid, thus reducing turbulence and entropy. This reduces gas expansion and allows for a workable fluid velocity.

With further reference to the system of FIG. 1, as an example, the catheter 102 is connected to a console 100. The console 100 contains the tank that supplies the cryogen. The console 100 may include precooling and defrost features. The console 100 and/or the catheter 102 include valving and plumbing to deliver the cryogen under pressure, e.g., delivering low pressure to the distal tip 112 of the catheter 102. There may be sensors within the console 100 and/or the catheter 102 to measure the temperature of the cryogen and/or the tissue. There may be a feedback loop for metered control of cryogen dosing. A pedal 106 may be used to control the cryogen delivery, or the cryogen delivery may be timed for a predetermined dosage. The distal tip 112 may be open-ended and/or include radial apertures. The console 100 may include software and/or hardware with safety features. The console 100 may include an interactive user interface. The console 100 may include control settings for a cryospray therapy procedure. The console 100 may include cryospray procedure profiles for pre-determined delivering of cryospray.

Figure 2:
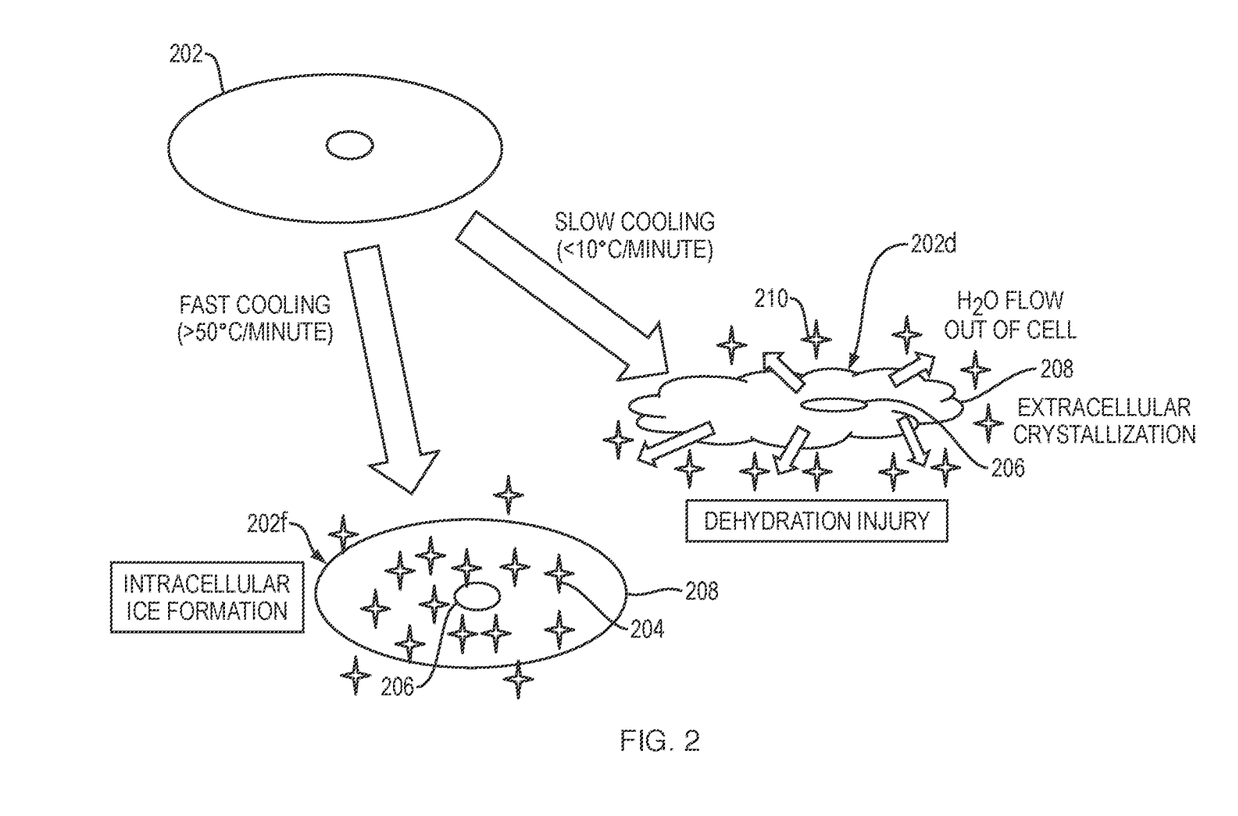
FIG. 2 illustrates aspects of cooling induced cellular change with a closed cryoprobe example, compared to cryospray treatment in accordance with an embodiment of the present disclosure.

With reference to FIG. 2, a comparison of the rate at which the target tissue temperature is reduced is illustrated between an open cryospray system in accordance with the present disclosure and a closed cryoprobe system. The difference between the systems and mechanisms of action is believed to directly relate to the cryotherapy results. For example, a closed-end cryoablation probe typically utilizes a Joule-Thomson effect to lower the temperature of compressed gases (e.g., argon, nitrogen, nitrous oxide, carbon dioxide) to below −40° C. This process drives a slow cooling of targeted tissue cells 202 over a period of several to tens of minutes at a relatively slow rate that might be less than 10° C. per minute. During this process, water 210 is osmotically removed from the cells into the intercellular, resulting in a dehydrated cell 202d. This may also cause cell shrinkage and death due to dehydration effects.

Conversely, in various embodiments of cryospray techniques according to the present disclosure, utilizing non-contact, opened-end approaches for treatment of target tissue, relatively faster cooling times are obtainable. When a cryogen (e.g., liquid nitrogen ($LN_2$)) is sprayed upon a targeted tissue cell 202, flash freezing of the region occurs. It is believed that this mechanism of action and rate of cooling has particularly beneficial application in the treatment of wounds, such as chronic wounds. A flash frozen cell 202f results in the formation of intracellular ice crystals 204 within the impacted tissue before cellular dehydration can occur. These ice crystals 204 further aggregate during the thawing process thereby disrupting intracellular organelles such as mitochondria 206 and endoplasmic reticulum while leaving the cell wall 208 intact. The disruption of the energy-producing organelles leads to cell death. The ablated flash frozen cells 202f lose their cellular attachments or become apoptotic and disintegrate or "slough off" of the membrane wall. Because collagen and elastin fibers are less sensitive to the effects of cryotherapy than are epithelial cells, the tissue structure remains intact.

Figure 3:
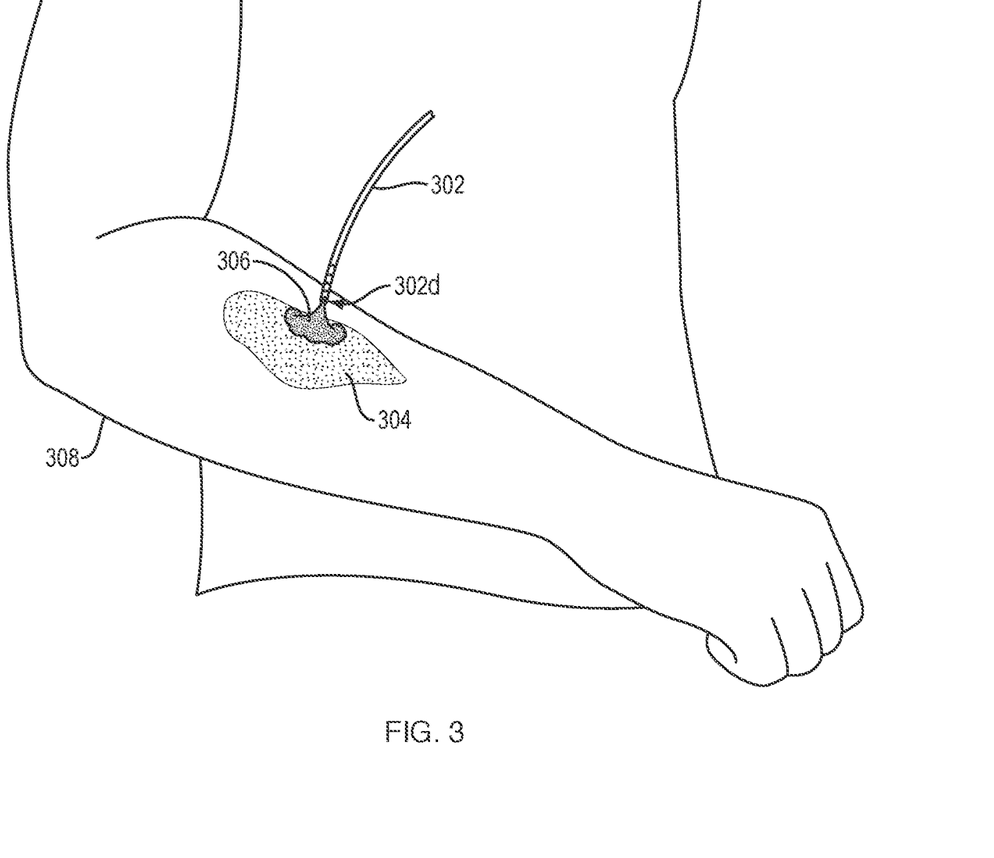
FIG. 3 illustrates treating a wound in accordance with an embodiment of the present disclosure.

In one embodiment of a method of treatment, with reference to FIG. 3, a catheter 302 is introduced in proximity to a wound 304 (on, e.g., the epidermis of an arm 308). The distal tip 302d of catheter is positioned within the range of about 10 mm to about 15 mm from the surface of the wound 304. A substantially perpendicular orientation of the distal tip 304d with respect to the surface of the wound 304 allows for an equal distribution cryospray 306 coverage of the wound 304. The cryospray is created by supplying the catheter 304 with a cryogen. The wound 304 is treated with cryospray 306 for a specific duration and it may be treated with multiple durational sessions of cryospray 306 during a procedure.

Precise control of cryospray dosage upon the wound may be necessary to produce a repeatable healing effect in different individuals with similar wounds. One approach is to use a catheter system, as described above, that consists, e.g., of a console with a liquid-nitrogen source with associated valves and control electronics to supply the $LN_2$ from the source and through the catheter to an end-spray nozzle. A controlled dose of $LN_2$ is then sprayed upon a tissue region, e.g., a 2 cm by 2 cm region of the wound, such that the surface layer(s) of tissue is flash frozen to a temperature of about −20° C. at a depth of about 1 mm.

Figure 4:
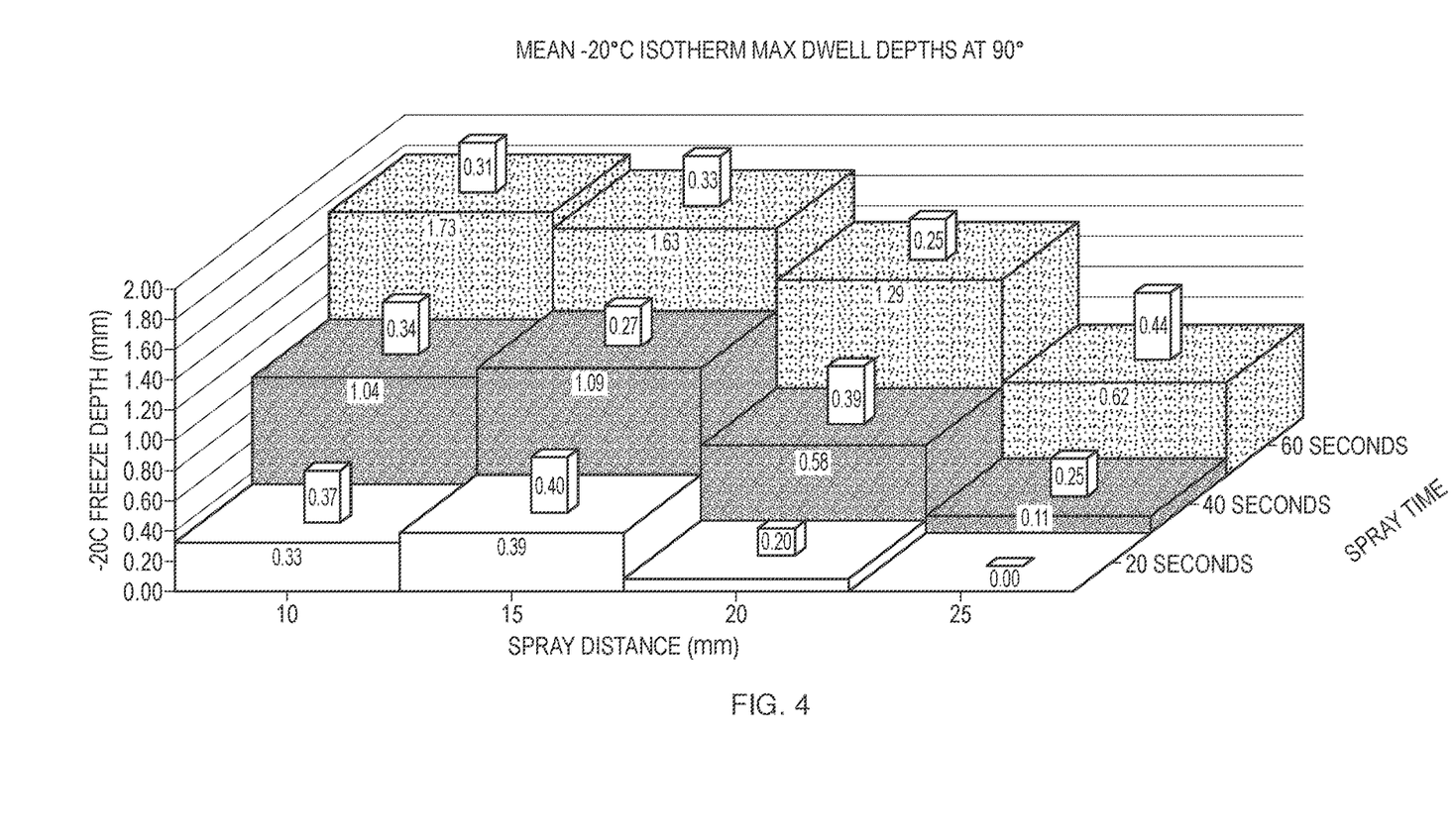
FIG. 4 displays exemplary data of cryospray distance versus freeze depth versus spray time in accordance with an embodiment of the present disclosure.

FIG. 4 displays an exemplary isotherm of the freeze depth, spray distance, and spray time that may be used to achieve a mean of −20° C. (with standard deviations) with embodiments of cryospray systems and methods in accordance with the present disclosure. These results were achieved in a 37° C. tissue-mimicking gel. Obtaining a −20° C. freeze up to a depth of about 1 mm may be accomplished with a cryospray catheter at distance of about 10 mm to about 15 mm from the target surface at a 90° incidence angle and for a duration of about 40 seconds.

A method for treating a wound may include a medical professional directing a distal tip of a catheter toward the wound. The distal tip may be angled perpendicular to a surface of the wound. The catheter may be supplied with a cryogen. The distal tip may be positioned within the range of about 10 mm to about 15 mm from the surface of the wound. The wound may be sprayed for a duration of about 40 seconds. The wound may be sprayed until a region of an approximate square surface of about 2 cm by about 2 cm and by about 1 mm of depth of the wound is about −20° C. A region of the wound may be cooled at more than about 50° C. per minute. Intracellular ice crystals may be formed within the tissue. An effective treatment may include an extracellular matrix of a tissue of the wound being maintained. An effective treatment may include a tissue of the wound being flash frozen. An effective treatment may include at least a region of the wound being remodeled. An effective treatment may include an undesirable tissue of the wound being ablated and possibly removed. The cryogen may be liquid nitrogen, liquid argon, liquid oxygen, liquid nitrous oxide, and/or liquid carbon dioxide.

Wounds may be treated within a body lumen of a patient by inserting a cryocatheter into the patient. The catheter is placed within a patient such that the distal tip is in proximity to the target tissue. A medical professional may visualize placement of the distal tip of the catheter via a camera in an endoscope and/or through flouroscopy. With the distal tip in position, the medical professional may introduce cryogen into the catheter. When the cryogen reaches the distal end of catheter it is sprayed out of the distal tip and/or the radial holes towards the target tissue. The medical professional may spray cryogen from the distal tip of the catheter parallel to a longitudinal axis of the catheter, and/or spray cryogen from a plurality of radial apertures at the distal tip of the catheter perpendicular to the longitudinal axis. Freezing of the target tissue is apparent to the medical professional by the acquisition of a white color, referred to as cryofrost, by the target tissue. The white color, resulting from surface frost, indicates the onset of mucosal or other tissue freezing sufficient to initiate destruction/ablation of the diseased or abnormal tissue. The operator may use a system timer to freeze for a specified duration once initial cryofrost is achieved in order to control the depth of injury. The medical professional may observe the degree of freezing and stop the spray as soon as the surface achieves the desired whiteness of color. The operator may monitor the target tissue to determine when cryofrost has occurred via the camera integrated into the endoscope. The operator may manipulate the catheter to freeze the target tissue. Once the operation is complete, the catheter, endoscope, and any other instruments such as a cryodecompression tube are withdrawn from the patient.

All of the devices and/or methods disclosed and claimed herein can be made and executed without undue experimentation in light of the present disclosure. While the devices and methods of this disclosure have been described in terms of exemplary embodiments, it will be apparent to those of skill in the art that variations can be applied to the devices and/or methods and in the steps or in the sequence of steps of the methods described herein without departing from the concept, spirit and scope of the disclosure. All such similar substitutes and modifications apparent to those skilled in the art are deemed to be within the spirit and scope of the present disclosure as defined by the appended claims.

What is claimed is:

1. A method of treating a wound comprising:
directing a distal tip of a cryospray catheter toward the wound;
orienting the distal tip of the catheter at an angle relative to a surface of the wound;
supplying cryogen to the distal tip of the catheter; and
spraying cryogen from the distal tip onto a tissue region of the wound at a distance from the wound, at a temperature of the cryogen, and for a duration of spraying, which are sufficient for effective treatment of the tissue region, until a temperature of an approximate square surface of the tissue region of the wound, about 2 cm long by about 2 cm wide, is about −20° C. to a depth from the surface of the wound,
wherein the duration is between about 20 seconds and about 60 seconds,
wherein the depth is more than 0.5 mm and up to about 1 mm.

2. The method of claim 1, wherein the distance ranges from about 10 mm to about 15 mm.

3. The method of claim 1, wherein the depth is about 1 mm.

4. The method of claim 1, wherein the effective treatment of the tissue region comprises forming intracellular ice crystals within the tissue region of the wound.

5. The method of claim 1, wherein the effective treatment of the tissue region comprises maintaining an extracellular matrix of tissue within the tissue region of the wound.

6. The method of claim 1, wherein the effective treatment of the tissue region comprises flash freezing a portion of the tissue region of the wound.

7. The method of claim 1, wherein the effective treatment of the tissue region comprises remodeling at least the tissue region of the wound.

8. The method of claim 1, wherein the effective treatment of the tissue region comprises ablating injured or damaged tissue within the tissue region of the wound.

9. The method of claim 1, further comprising the step of removing tissue from the tissue region of the wound that has been treated.

10. The method of claim 1, wherein the cryogen is selected from the group consisting of liquid nitrogen, liquid argon, liquid oxygen, liquid nitrous oxide, and liquid carbon dioxide.

11. The method of claim 1, wherein the angle is substantially perpendicular.

12. The method of claim 1, wherein the wound is selected from the group consisting of a burn, an ulcer, a chronic wound, and a lesion.

13. The method of claim 1, wherein the wound is on an external surface of a patient's body.

14. A method of treating a wound comprising:
directing a distal tip of a cryospray catheter toward a wound;
orienting the distal tip of the catheter at an angle relative to at least one surface layer of the wound; and
spraying cryogen from the distal tip onto the at least one surface layer of the wound at a distance from the wound, at a temperature of the cryogen, and for a duration of spraying, which are sufficient for effective treatment of the at least one surface layer at a tissue temperature of about −20° C. up to a depth from a surface of the wound,
wherein the duration is between about 20 seconds and about 60 seconds,
wherein the depth is more than 0.5 mm and up to about 1 mm.

15. The method of claim 14, wherein spraying cryogen further comprises spraying until a temperature of an approximate square region of the at least one surface layer, about 2 cm long by about 2 cm wide, is about −20° C. to a depth of more than 0.5 mm and up to about 1 mm.

16. The method of claim 14, wherein the effective treatment of the tissue region comprises flash freezing the at least one surface layer.

17. The method of claim 14, wherein the effective treatment of the tissue region comprises leaving a plurality of collagen fibers and an extra-cellular matrix of a region of the wound intact.

18. A method of treating a wound comprising:
inserting a cryospray catheter within a body lumen;
orienting a distal tip of the catheter at an angle relative to a region of exposed tissue of a wound within the body lumen;
supplying cryogen to the distal tip of the catheter; and
spraying cryogen from the distal tip onto the exposed tissue region of the wound at a distance from the wound, at a temperature of the cryogen, and for a duration of spraying, which are sufficient for effective treatment of the tissue region, until a temperature of an approximate square surface of the tissue region of the wound, about 2 cm long by about 2 cm wide, is about −20° C. to a depth from a surface of the wound,
wherein the duration is between about 20 seconds and about 60 seconds,
wherein the depth is more than 0.5 mm and up to about 1 mm.

19. The method of claim 18, wherein the effective treatment of the exposed tissue region comprises ablating injured or damaged tissue.

20. The method of claim 18, wherein the spraying step includes one or both of spraying cryogen from the distal tip of the catheter parallel to a longitudinal axis of the catheter, and spraying cryogen from a plurality of radial apertures at the distal tip of the catheter perpendicular to the longitudinal axis.

* * * * *